(12) United States Patent
Vrba

(10) Patent No.: US 8,083,689 B2
(45) Date of Patent: Dec. 27, 2011

(54) DISTAL PROTECTION GUIDEWIRE WITH NITINOL CORE

(75) Inventor: Anthony C. Vrba, Maple Grove, MN (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 1039 days.

(21) Appl. No.: 11/608,619

(22) Filed: Dec. 8, 2006

(65) Prior Publication Data

US 2007/0100374 A1 May 3, 2007

Related U.S. Application Data

(63) Continuation of application No. 10/318,907, filed on Dec. 13, 2002, now abandoned.

(51) Int. Cl.
*A61M 25/00* (2006.01)

(52) U.S. Cl. ........................................ 600/585

(58) Field of Classification Search ............... 600/585; 604/164.13
See application file for complete search history.

(56) References Cited

U.S. PATENT DOCUMENTS

| | | | |
|---|---|---|---|
| 3,472,230 A | 10/1969 | Fogarty | |
| 3,952,747 A | 4/1976 | Kimmell, Jr. | |
| 3,996,938 A | 12/1976 | Clark, III | |
| 4,425,908 A | 1/1984 | Simon | |
| 4,643,184 A | 2/1987 | Mobin-Uddin | |
| 4,662,885 A | 5/1987 | DiPisa, Jr. | |
| 4,706,671 A | 11/1987 | Weinrib | |
| 4,723,549 A | 2/1988 | Wholey et al. | |
| 4,790,812 A | 12/1988 | Hawkins, Jr. et al. | |
| 4,790,813 A | 12/1988 | Kensey | |
| 4,794,928 A | 1/1989 | Kletschka | |
| 4,857,045 A | 8/1989 | Rydell | |
| 4,873,978 A | 10/1989 | Ginsburg | |
| 4,886,061 A | 12/1989 | Fischell et al. | |
| 4,969,891 A | 11/1990 | Gewertz | |
| 5,011,488 A | 4/1991 | Ginsburg | |
| 5,071,407 A | 12/1991 | Termin et al. | |
| 5,133,733 A | 7/1992 | Rasmussen et al. | |
| 5,160,342 A | 11/1992 | Reger et al. | |
| 5,192,286 A | 3/1993 | Phan et al. | |
| 5,324,304 A | 6/1994 | Rasmussen | |
| 5,329,942 A | 7/1994 | Gunther et al. | |
| 5,365,943 A * | 11/1994 | Jansen | 600/585 |
| 5,370,657 A | 12/1994 | Irie | |
| 5,415,630 A | 5/1995 | Gory et al. | |
| 5,419,774 A | 5/1995 | Willard et al. | |
| 5,462,529 A | 10/1995 | Simpson et al. | |
| 5,536,242 A | 7/1996 | Willard et al. | |
| 5,549,626 A | 8/1996 | Miller et al. | |
| 5,662,671 A | 9/1997 | Barbut et al. | |

(Continued)

FOREIGN PATENT DOCUMENTS

WO 96/01591 A1 1/1996

*Primary Examiner* — Jeffrey G Hoekstra
(74) *Attorney, Agent, or Firm* — Seager, Tufte & Wickhem LLC

(57) ABSTRACT

A guidewire having a proximal section, a distal section, and a transition section is disclosed. In one exemplary embodiment of the present invention, the proximal section may be formed of a relatively stiff, inelastic material, whereas the distal section may be formed of a relatively flexible, elastic material having super-elastic properties. A coupling member may be placed adjacent to the transition section to secure the proximal and distal sections together.

24 Claims, 1 Drawing Sheet

U.S. PATENT DOCUMENTS

| | | | |
|---|---|---|---|
| 5,669,933 A | 9/1997 | Simon et al. | |
| 5,769,816 A | 6/1998 | Barbut et al. | |
| 5,779,716 A | 7/1998 | Cano et al. | |
| 5,800,457 A | 9/1998 | Gelbfish | |
| 5,800,525 A | 9/1998 | Bachinski et al. | |
| 5,807,398 A | 9/1998 | Shaknovich | |
| 5,814,064 A | 9/1998 | Daniel et al. | |
| 5,827,324 A * | 10/1998 | Cassell et al. | 606/200 |
| 5,833,650 A | 11/1998 | Imran | |
| 5,848,964 A | 12/1998 | Samuels | |
| 5,911,734 A | 6/1999 | Tsugita et al. | |
| 6,066,149 A | 5/2000 | Samson et al. | |
| 6,066,158 A | 5/2000 | Engelson et al. | |
| 6,142,987 A | 11/2000 | Tsugita | |
| 6,152,946 A | 11/2000 | Broome et al. | |
| 6,168,579 B1 | 1/2001 | Tsugita | |
| 6,171,327 B1 | 1/2001 | Daniel et al. | |
| 6,179,861 B1 | 1/2001 | Khosravi et al. | |
| 6,203,561 B1 | 3/2001 | Ramee et al. | |
| 6,206,868 B1 | 3/2001 | Parodi | |
| 6,221,006 B1 | 4/2001 | Dubrul et al. | |
| 6,277,139 B1 | 8/2001 | Levinson et al. | |
| 6,488,637 B1 * | 12/2002 | Eder et al. | 600/585 |
| 6,605,102 B1 | 8/2003 | Mazzocchi et al. | |

\* cited by examiner

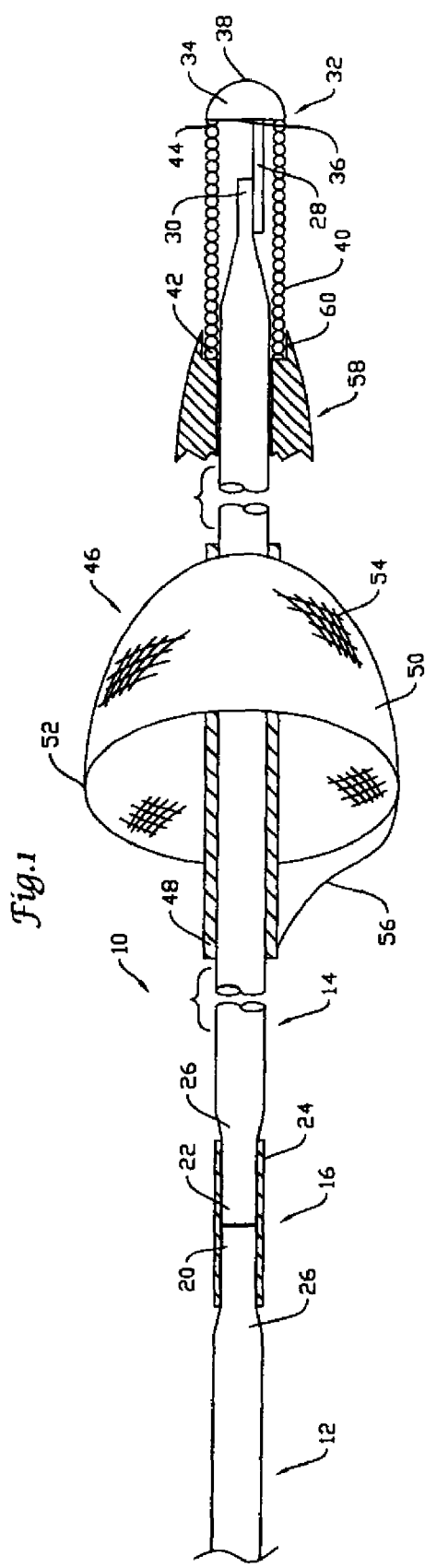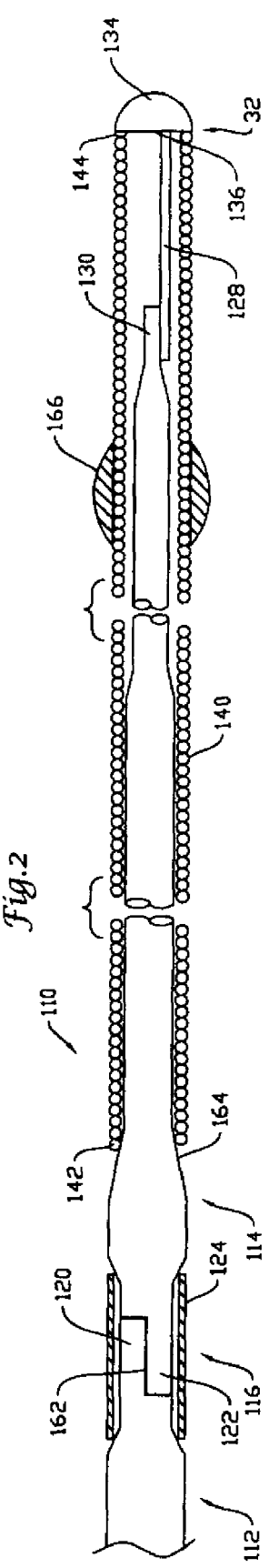

DISTAL PROTECTION GUIDEWIRE WITH NITINOL CORE

This is a continuation of U.S. application Ser. No. 10/318,907 filed Dec. 13, 2002.

FIELD OF THE INVENTION

The present invention relates generally to the field of intravascular guidewires. More specifically, the present invention pertains to guidewires having super-elastic properties.

BACKGROUND OF THE INVENTION

Guidewires are frequently used to advance intravascular devices such as stent delivery catheters, angioplasty catheters, and atherectomy catheters within a patient's vasculature. Such devices generally include a stiff proximal section to facilitate pushability and torqueability, and a flexible distal section for improved trackability. In some cases, the distal section of the guidewire may have a reduced profile capable of placement beyond a lesion or other stenosis within the body.

One important aspect of guidewire designs is the ability of the distal section to undergo significant bending within the body without permanently deforming the guidewire. Kinking results when the stress within the guidewire exceeds the elastic limit of the material, causing the material to plastically deform. As a result, a residual strain is imparted to the guidewire preventing it from fully recovering to its original shape. In certain circumstances, the inability of the guidewire to return to its original shape may diminish the performance and durability characteristics of the guidewire.

SUMMARY OF THE INVENTION

The present invention relates generally to guidewires having super-elastic properties. In an exemplary embodiment of the present invention, a guidewire comprises a proximal section formed of a first material, and a distal section formed of a second material different from the first material. The proximal section of the guidewire may be formed of a relatively stiff inelastic material, whereas the distal section may be formed of a relatively flexible, elastic material. In some embodiments, the distal section may be formed of a super-elastic material such as nickel-titanium alloy. A coupling member may be attached to the guidewire adjacent a transition section, securing the proximal and distal sections together.

BRIEF DESCRIPTION OF THE DRAWINGS

FIG. 1 is a plan view of an intravascular guidewire in accordance with an exemplary embodiment of the present invention, showing an embolic protection filter advanced along the guidewire; and FIG. 2 is a plan view of an intravascular guidewire in accordance with another exemplary embodiment of the present invention.

DETAILED DESCRIPTION OF THE INVENTION

The following description should be read with reference to the drawings, in which like elements in different drawings are numbered in like fashion. The drawings, which are not necessarily to scale, depict selected embodiments and are not intended to limit the scope of the invention. Although examples of construction, dimensions, and materials are illustrated for the various elements, those skilled in the art will recognize that many of the examples provided have suitable alternatives that may be utilized.

FIG. 1 is a plan view of an intravascular guidewire in accordance with an exemplary embodiment of the present invention. Guidewire 10 includes a proximal section 12, a distal section 14, and a transition section 16 securing the proximal section 12 to the distal section 14. Guidewire 10 is configured to support one or more intravascular devices thereon, such as the embolic protection filter 46 illustrated in FIG. 1.

The proximal section 12 of guidewire 10 may be formed of a relatively stiff, inelastic material to enhance the pushability and torqueability characteristics of the guidewire, and to support the weight of various intravascular devices (e.g. balloon catheters, stent delivery catheters, etc.) thereon. Proximal section 12 may be formed of a metal such as type 304V stainless steel or platinum.

The distal section 14 of guidewire 10 may be formed of a relatively flexible, elastic material configured to impart flexibility to the guidewire for enhanced tracking through the tortuous vasculature. The distal section 14 may be formed from a material having different mechanical properties than the proximal section 12 of the guidewire 10. For example, the distal section 14 may be formed from a material having a lower modulus of elasticity than the proximal section 12, thereby imparting greater flexibility to the distal section 14. In one exemplary embodiment, the distal section 14 may comprise a super-elastic and/or linear-elastic material such as nickel-titanium alloy (Nitinol). Nickel-titanium alloy exhibits pseudo-elastic capabilities at body temperature (37° C.), allowing it to undergo substantial bending with relatively little residual strain. Unlike more commonly used materials such as stainless steel, the use of super-elastic materials such as Nitinol allows the distal section 14 to bend significantly without permanently (i.e. plastically) deforming.

Guidewire 10 further includes a transition section 16 forming a joint between the proximal and distal sections 12, 14. As shown in FIG. 1, for example, the distal end 20 of the proximal section 12 may be coupled to the proximal end 22 of the distal section 14, forming a butt joint therebetween. The proximal and distal sections 12, 14 of the guidewire 10 may be bonded together by adhesive, welding (e.g. resistance, laser, ultrasonic), soldering, brazing, or any other suitable bonding technique.

In certain embodiments, guidewire 10 may include a coupling member 24 further securing the proximal section 12 to the distal section 14. The coupling member 24 may comprise a tubular member or wire coil having an inner diameter configured to receive the distal end 20 of the proximal section 12 and the proximal end 22 of the distal section 14. The coupling member 24 may be formed from a metal or metal alloy, including stainless steel, nickel-titanium alloy, nickel-chromium alloy, nickel-chromium-iron alloy, nickel-chromium-molybdenum, cobalt alloy, or nickel. For example, in bonding a stainless steel proximal section 12 to a nickel-titanium distal section 14, a nickel-chromium-molybdenum based alloy such as INCONEL 625, ALLOY C276 or ALLOY B2 may be used. INCONEL 625 is commercially available from the California Fine Wire Company of Grover Beach, Calif. ALLOY C276 and B2 are commercially available from the Fort Wayne Metals Research Products Corporation of Fort Wayne, Ind.

In an alternative embodiment, the coupling member 24 may comprise a polymeric material that can be heat shrunk adjacent the ends 20, 22 of the proximal and distal sections 12, 14. For example, a tubular segment formed of polytetraflouroethylene (PTFE) can be placed adjacent the ends 20, 22 of the two sections 12, 14 and heated to a sufficient temperature, causing the material to flow onto the ends 20, 22. In yet another embodiment, the coupling member 24 may include a solder material that can be reflowed adjacent the ends 20, 22 of the proximal and distal sections 12, 14.

In those embodiments utilizing a coupling member 24, the ends 20, 22 of the proximal and distal sections 12, 14 may be tapered or reduced in diameter such that the profile of the guidewire 10 at the transition section 16 is substantially similar to the profile of the proximal and distal sections 12, 14 immediately adjacent the transition section 16. As shown in FIG. 1, for example, the ends 20, 22 of the proximal and distal sections 12, 14 may include a necked-down portion 26 reducing the outer diameter of the sections 12, 14 at the transition section 16.

The distal section 14 may also include a shaping ribbon 28. The shaping ribbon 28 connects the distal end 30 of the distal section 14 to a coil tip 34 disposed at the distal end 32 of the guidewire 10. The shaping ribbon 28 may be formed of metal (e.g. type 304V stainless steel), a polymer, or any other suitable material.

Coil tip 34 is generally circular in shape, and includes a proximal portion 36 forming a rearwardly facing shoulder, and a distal portion 38. The coil tip 34 may be substantially round, and may include a hydrophilic coating to reduce tissue damage within the body.

Guidewire 10 may also include a wire coil 40 disposed at least in part about the distal section 14. The wire coil 40 may be attached at a proximal end 42 to the distal section 14, and at a distal end 44 to the proximal portion 36 of coil tip 34. The wire coil 40 may be formed from a single, continuous strand of wire helically disposed about the distal section 14. In certain embodiments, the wire coil 40 may comprise a radiopaque material such as gold, platinum, or tantalum, allowing the operator to fluoroscopically judge the location of the guidewire 10 within the body.

An intravascular device such as the embolic protection filter 46 depicted in FIG. 1 may be placed on the guidewire 10. The embolic protection filter 46 may include a tubular base member 48, which allows the filter 46 to slide and rotate about the guidewire 10. In use, the guidewire 10 may be percutaneously inserted into a blood vessel, and advanced to a desired location within the body (e.g. a coronary artery). Once positioned, the embolic protection filter 46 can then be advanced over the guidewire 10 via a delivery catheter, and placed at a location downstream a lesion or other stenosis within the vessel. An intravascular device such as an angioplasty balloon can then be advanced along the guidewire 10 to a location upstream of the embolic protection filter 46 to perform a therapeutic procedure such as percutaneous transluminal coronary angioplasty. A stent may also be advanced along the guidewire 10 and deployed within the body, if desired.

In an alternative embodiment (not shown), the embolic protection filter 46 may be fixedly secured to the distal section 14 of the guidewire 10 prior to insertion within the patient. In a fixed configuration, the guidewire 10 and attached embolic protection filter are both loaded into the delivery catheter prior to being inserted into the body. The guidewire 10 and attached filter are simultaneously inserted into the body, and then advanced to the site of the lesion. Once positioned distal the lesion, the guidewire can then be used to advance other intravascular devices to the site.

To collect embolic debris dislodged during the therapeutic procedure, embolic protection filter 46 may include a filter mesh or membrane 50 coupled to a proximal support hoop 52. The proximal support hoop 52 forms a mouth or opening on the embolic protection filter 46, and is biased to radially expand within the vessel when removed from the delivery catheter. The filter mesh or membrane 50 may include several openings or pores 54 configured to filter embolic debris while permitting the perfusion of blood through the blood vessel. A tether line 56 connects the embolic protection filter 46 to the tubular base member 48.

Embolic protection filter 46 may further include a nose cone 58. Nose cone 58 is formed from an enlarged diameter distal portion of the tubular base member 48. The nose cone 58 is tapered distally to provide a relatively uniform profile transition between the proximal end 42 of the wire coil 40 and the embolic protection filter 46. A reduced inner diameter portion 60 on the distal end 62 of the nose cone 58 is adapted to slide over the proximal end 42 of the wire coil 40. In use, the proximal end 42 of the wire coil 40 acts as a distal stop, preventing the embolic protection filter 46 from being advanced beyond the distal end 32 of the guidewire 10.

FIG. 2 is a plan view of an intravascular guidewire in accordance with another exemplary embodiment of the present invention. Guidewire 110 includes a proximal section 112, a distal section 114, and a transition section 116. As with the embodiment described above with respect to FIG. 1, guidewire 110 is configured to support one or more intravascular devices thereon.

The proximal section 112 of guidewire 110 may comprise a relatively stiff, inelastic material (e.g. type 304V stainless steel), whereas the distal section 114 may comprise a relatively flexible, super-elastic material such as nickel-titanium alloy. The distal end 120 of the proximal section 112 may include a notch configured to align with a correspondingly dimensioned notch on the proximal end 122 of the distal section 114. Together, the notches form a lap joint 162 between the proximal and distal sections 112, 114.

A coupling member 124 may also be placed adjacent the ends 120, 122 of the proximal and distal sections 112, 114 at the transitional section 116. In those embodiments utilizing a coupling member 124, the ends 120, 122 of the proximal and distal sections 112, 114 may be tapered or reduced in diameter such that the profile of the guidewire 110 at the transition section 116 is substantially similar to the profile of the proximal and distal sections 112, 114 immediately adjacent the transition section 116.

A wire coil 140 may be placed about a portion of the distal section 114. Wire coil 140 has a proximal end 142 and a distal end 144. The proximal end 142 of wire coil 140 may be attached to a shoulder 164 located on the distal section 114 of the guidewire 110. The distal end 144 of wire coil 140, in turn, may be attached to the proximal portion 136 of the coil tip 134. A shaping ribbon 128 connecting the distal end 130 of the distal section 114 to the proximal portion 136 of the coil tip 134 may also be used, if desired.

Guidewire 110 further includes a distal stop 166 disposed about a portion of the distal section 114. Distal stop 166 comprises an object having an outer diameter slightly larger than the inner diameter of the intravascular device. In use, the distal stop 166 prevents movement of the intravascular device beyond the distal end 132 of the guidewire 110.

Attachment of the distal stop 166 to the guidewire 110 may be accomplished by any number of suitable attachment means, including crimping, soldering, brazing, welding, adhesion or any combination thereof. Furthermore, the distal stop 166 may be formed from any number of suitable materials, such as stainless steel or nickel-titanium alloy. In one implementation, the distal stop 166 may be formed by heat bonding a polymeric object about the distal section 114.

Although the exemplary embodiments illustrated in FIGS. 1-2 depict a guidewire 10, 110 having a solid core (i.e. solid cross-section), it should be understood that other configurations are possible without deviating from the scope of the invention. For example, the proximal and distal sections may have a hollow cross-sectional area, forming a guide catheter or the like.

Having thus described the several embodiments of the present invention, those of skill in the art will readily appreciate that other embodiments may be made and used which fall within the scope of the claims attached hereto. Numerous advantages of the invention covered by this document have been set forth in the foregoing description. It will be understood that this disclosure is, in many respects, only illustrative. Changes may be made in details, particularly in matters of shape, size and arrangement of parts without exceeding the scope of the invention.

What is claimed is:

1. A guidewire, comprising:
    an elongate shaft including a proximal section having a distal end, a distal section having a proximal end, and a transition section, the proximal section comprising a first material, the distal section comprising a second material different from the first material, the transition section includes the distal end of the proximal section abutting the proximal end of the distal section;
    a coupling member attached adjacent to the transition section, said coupling member configured to secure the proximal section to the distal section; and
    further comprising a distal stop disposed about a portion of said distal section.

2. The guidewire of claim 1, further comprising an embolic protection filter disposed on the shaft.

3. The guidewire of claim 1, wherein the proximal section is comprised of stainless steel.

4. The guidewire of claim 1, wherein the distal section is comprised of nickel-titanium alloy.

5. The guidewire of claim 1, wherein the distal section is comprised of a super-elastic material.

6. The guidewire of claim 1, wherein the distal section is comprised of a linear-elastic material.

7. The guidewire of claim 1, wherein the transition section includes a joint between the proximal and distal sections.

8. The guidewire of claim 7, wherein said joint is a butt joint.

9. The guidewire of claim 7, wherein said joint is a lap joint.

10. The guidewire of claim 1, wherein the transition section includes a necked-down portion.

11. The guidewire of claim 1, wherein the coupling member includes a tubular member.

12. The guidewire of claim 1, wherein the coupling member includes a polymeric member heat shrunk adjacent to the transition section.

13. The guidewire of claim 1, further comprising a wire coil disposed about a portion of said distal section.

14. The guidewire of claim 13, wherein said wire coil comprises a radiopaque material.

15. A guidewire, comprising:
    an elongate shaft including a proximal section, a distal section, and a transition section, the proximal section comprising a first material, the distal section comprising a second material different from the first material, the transition section including a necked-down portion;
    a coupling member attached adjacent to the transition section, said coupling member configured to secure the proximal section to the distal section, and further comprising a distal stop disposed about a portion of said distal section.

16. The guidewire of claim 15 further comprising an embolic protection filter disposed on the shaft.

17. The guidewire of claim 15, wherein the proximal section is comprised of stainless steel.

18. The guidewire of claim 15, wherein the distal section is comprised of nickel-titanium alloy.

19. The guidewire of claim 15, wherein the transition section includes a joint between the proximal and distal sections.

20. The guidewire of claim 15, wherein the coupling member includes a tubular member.

21. The guidewire of claim 15, wherein the coupling member includes a polymeric member heat shrunk adjacent to the transition section.

22. The guidewire of claim 15, further comprising a wire coil disposed about a portion of said distal section.

23. The guidewire of claim 22, wherein said wire coil comprises a radiopaque material.

24. A guidewire, comprising:
    an elongate shaft including a proximal section formed of a relatively stiff, elastic material, a distal section formed of a relatively flexible, elastic material, and a transition section including a necked-down portion forming a joint between the proximal and distal sections;
    a coupling member attached adjacent to the transition section;
    an embolic protection filter disposed on the shaft; and
    further comprising a distal stop disposed about a portion of said distal section.

* * * * *